US010314749B2

(12) United States Patent
Mueller et al.

(10) Patent No.: US 10,314,749 B2
(45) Date of Patent: Jun. 11, 2019

(54) WAIST ASSEMBLY HAVING APERTURED LAYER AND NON-APERTURED LAYER FOR ABSORBENT ARTICLES

(71) Applicant: KIMBERLY-CLARK WORLDWIDE, INC., Neenah, WI (US)

(72) Inventors: Justin M. Mueller, Oshkosh, WI (US); KyungSik Jang, Daejeon (KR); JaeHong Lee, Gyeonggi-do (KR); WenTong Lay, Appleton, WI (US); Gabriel F. Botero, Antioquia (CO); Blake A. Hondl, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 14/898,659

(22) PCT Filed: Sep. 26, 2014

(86) PCT No.: PCT/US2014/057589
§ 371 (c)(1),
(2) Date: Dec. 15, 2015

(87) PCT Pub. No.: WO2016/048337
PCT Pub. Date: Mar. 31, 2016

(65) Prior Publication Data
US 2017/0189244 A1 Jul. 6, 2017

(51) Int. Cl.
*A61F 13/49* (2006.01)
*A61F 13/496* (2006.01)
(Continued)

(52) U.S. Cl.
CPC .... *A61F 13/49012* (2013.01); *A61F 13/4902* (2013.01); *A61F 13/496* (2013.01);
(Continued)

(58) Field of Classification Search
CPC ............ A61F 13/49012; A61F 13/4902; A61F 13/49466; A61F 13/496; A61F 13/5146;
(Continued)

(56) References Cited

U.S. PATENT DOCUMENTS 4,887,602 A    12/1989  O'Leary
4,935,287 A *  6/1990  Johnson .................... B32B 5/04
                                                    428/152
(Continued)

FOREIGN PATENT DOCUMENTS

EP          0967953 B1      9/1998
JP          H03251245 A    11/1991
WO          0197739 A1     12/2001

OTHER PUBLICATIONS

International Preliminary Report on Patentability issued in International Patent Application No. PCT/US2014/57589 dated Aug. 22, 2016.
(Continued)

*Primary Examiner* — Adam Marcetich
*Assistant Examiner* — Jessica R Arble
(74) *Attorney, Agent, or Firm* — Armstrong Teasdale

(57) ABSTRACT

An absorbent article having a front region, a back region, and a crotch region extending between and connecting the front region and the back region generally includes an absorbent assembly extending longitudinally between the front region and the back region, and a waist assembly attached to the absorbent assembly along the front region and the back region. The absorbent assembly includes an inner layer for facing a wearer, an outer layer for facing away from the wearer, and an absorbent structure disposed between the inner and outer layers. The waist assembly defines a waist opening of the absorbent article when the article is in a wear configuration, and includes an elastic laminate including a non-apertured body-facing layer, an
(Continued)

apertured garment-facing layer, and an elastic layer disposed between the body-facing layer and the garment-facing layer.

23 Claims, 5 Drawing Sheets

(51) Int. Cl.
    *A61F 13/514*     (2006.01)
    *A61F 13/494*     (2006.01)

(52) U.S. Cl.
    CPC .... *A61F 13/49466* (2013.01); *A61F 13/5146* (2013.01); *A61F 13/51462* (2013.01); *A61F 13/51496* (2013.01); *A61F 2013/49025* (2013.01)

(58) Field of Classification Search
    CPC .......... A61F 13/51462; A61F 13/51496; A61F 2013/49025
    See application file for complete search history.

(56) References Cited

U.S. PATENT DOCUMENTS

| | | | |
|---|---|---|---|
| 5,569,234 A * | 10/1996 | Buell | A61F 13/49009 604/358 |
| 5,571,096 A | 11/1996 | Dobrin et al. | |
| 5,691,040 A * | 11/1997 | Barbeau | A41D 31/0027 2/456 |
| 5,769,838 A | 6/1998 | Buell et al. | |
| 5,836,932 A | 11/1998 | Buell et al. | |
| 5,899,895 A | 5/1999 | Robles et al. | |
| 5,916,661 A | 6/1999 | Benson et al. | |
| 6,039,906 A * | 3/2000 | Sageser | A61F 13/49011 264/156 |
| 6,307,120 B1 | 10/2001 | Glaug | |
| 6,878,647 B1 | 4/2005 | Rezai et al. | |
| 6,994,761 B2 | 2/2006 | Klemp et al. | |
| 7,169,137 B2 | 1/2007 | Shimada | |
| 7,806,883 B2 | 10/2010 | Fossum et al. | |
| 7,855,316 B2 | 12/2010 | Meyer et al. | |
| 8,029,484 B2 | 10/2011 | DiCarlo | |
| 8,153,857 B2 | 4/2012 | Mirle et al. | |
| 8,343,411 B2 * | 1/2013 | Arora | A61F 13/15707 264/132 |
| 8,377,027 B2 | 2/2013 | Hughes et al. | |
| 8,500,710 B2 | 8/2013 | Takino et al. | |
| 2001/0049512 A1 | 12/2001 | Kawamura et al. | |
| 2003/0114817 A1 * | 6/2003 | Roessler | A61F 13/15699 604/378 |
| 2003/0120240 A1 * | 6/2003 | Buell | A61F 13/496 604/385.01 |
| 2004/0243089 A1 * | 12/2004 | Veith | A61F 13/49012 604/385.22 |
| 2006/0058772 A1 | 3/2006 | Karami | |
| 2009/0254057 A1 * | 10/2009 | Ceusters | A61F 13/49012 604/367 |
| 2011/0092942 A1 | 4/2011 | Ruman et al. | |
| 2011/0319853 A1 | 12/2011 | Yamashita et al. | |
| 2012/0277702 A1 * | 11/2012 | Raycheck | A61F 13/51496 604/367 |
| 2012/0330260 A1 * | 12/2012 | Bishop | A61F 13/4946 604/378 |
| 2013/0306226 A1 * | 11/2013 | Zink | A61F 13/15699 156/163 |
| 2015/0297423 A1 * | 10/2015 | Nelson | A61F 13/51478 604/365 |

OTHER PUBLICATIONS

International Search Report and Written Opinion of International Application No. PCT/US2014/057589, dated May 21, 2015, 12 pages.

* cited by examiner

WAIST ASSEMBLY HAVING APERTURED LAYER AND NON-APERTURED LAYER FOR ABSORBENT ARTICLES

FIELD

The field of the invention relates generally to waist assemblies for absorbent articles, and more specifically to waist assemblies having an apertured layer and a non-apertured layer.

BACKGROUND

Absorbent articles, such as diapers, incontinence garments, training pants, sanitary napkins, panty liners, and the like are well known in the art. These articles, which are often disposable, are capable of absorbing and retaining fluids and other bodily discharges. Some absorbent articles, such as pull-on type absorbent articles, include a central absorbent member and side panels extending from and interconnecting respective front and back regions of the absorbent member forming a waist assembly.

Some known absorbent articles include liquid impermeable side panels to prevent liquid discharged by a wearer from leaking through the side panels. Such side panels can be impervious to water vapor as well as liquid. Side panels that are impermeable to both liquids and water vapor can cause the absorbent article often to feel hot and clammy to the wearer, especially after a bodily discharge. Furthermore, the lack of permeability to both liquid and water vapor may cause irritation to the skin of the wearer around the waist. In addition to concerns over skin wellness, liquid impermeable side panels often lack aesthetic and tactile qualities desired in absorbent articles.

Other known side panels for absorbent articles are "breathable". Such side panels, which are typically constructed from nonwoven materials, are "breathable" in the sense that air can pass through the side panels. While often providing a more skin friendly product, breathable side panels often suffer from inadequate liquid impermeability. That is, breathable side panels often lack sufficient liquid impermeability to prevent bodily fluids from leaking through the side panels.

Additionally, it is often difficult for users (e.g., wearers, caregivers) of absorbent articles to readily determine if the article they are using has non-breathable or breathable side panels. That is, the articles having breathable side panels are often not readily discernible from articles having non-breathable outer covers. As mentioned above, breathable side panels often provide a skin-healthier product from the wearer's perspective as compared to non-breathable side panels.

Thus, there exists a need for an absorbent article including a waist assembly that is sufficiently water-vapor permeable to provide a healthy and comfortable product for the wearer, but that is also sufficiently liquid impermeable to inhibit bodily fluids from leaking through the waist assembly. Moreover, there exists a need for such an absorbent article configured to enhance the noticeability of the waist assembly's breathability to a user.

BRIEF DESCRIPTION

In one aspect, an absorbent article having a front region, a back region, and a crotch region extending between and connecting the front region and the back region generally comprises an absorbent assembly extending longitudinally between the front region and the back region, and a waist assembly attached to the absorbent assembly along the front region and the back region. The absorbent assembly includes an inner layer for facing a wearer, an outer layer for facing away from the wearer, and an absorbent structure disposed between the inner and outer layers. The waist assembly defines a waist opening of the absorbent article when the article is in a wear configuration, and includes an elastic laminate including a non-apertured body-facing layer, an apertured garment-facing layer, and an elastic layer disposed between the body-facing layer and the garment-facing layer.

In another aspect, an absorbent article having a front region, a back region, and a crotch region extending between and connecting the front region and the back region generally comprises an absorbent assembly extending longitudinally between the front region and the back region, and a waist assembly attached to the absorbent assembly along the front region and the back region. The absorbent assembly includes an inner layer for facing a wearer, an outer layer for facing away from the wearer, and an absorbent structure disposed between the inner and outer layers. The waist assembly defines a waist opening of the absorbent article when the article is in a wear configuration, and includes an elastic laminate including a non-apertured body-facing layer, an apertured garment-facing layer, and an elastic layer disposed between the body-facing layer and the garment-facing layer. The elastic laminate has a hydrostatic pressure of between about 4 millibar and about 20 millibar as determined by the 1-Drop Hydrostatic Pressure Test, and an air permeability of between about 310 cubic feet per minute and about 620 cubic feet per minute as determined by the Air Permeability Test.

In yet another aspect, an absorbent article having a front region, a back region, and a crotch region extending between and connecting the front region and the back region generally comprises an absorbent assembly extending longitudinally between the front region and the back region, and a waist assembly attached to the absorbent assembly along the front region and the back region. The absorbent assembly includes an inner layer for facing a wearer, an outer layer for facing away from the wearer, and an absorbent structure disposed between the inner and outer layers. The waist assembly defines a waist opening of the absorbent article when the article is in a wear configuration, and includes an elastic laminate including a non-apertured body-facing layer, an apertured garment-facing layer, and an elastic layer disposed between the body-facing layer and the garment-facing layer. The elastic laminate has a hydrostatic pressure of between about 7 millibar and about 17 millibar as determined by the 1-Drop Hydrostatic Pressure Test, and an air permeability of between about 260 cubic feet per minute and about 690 cubic feet per minute.

DETAILED DESCRIPTION OF THE DRAWINGS

Figure 1:
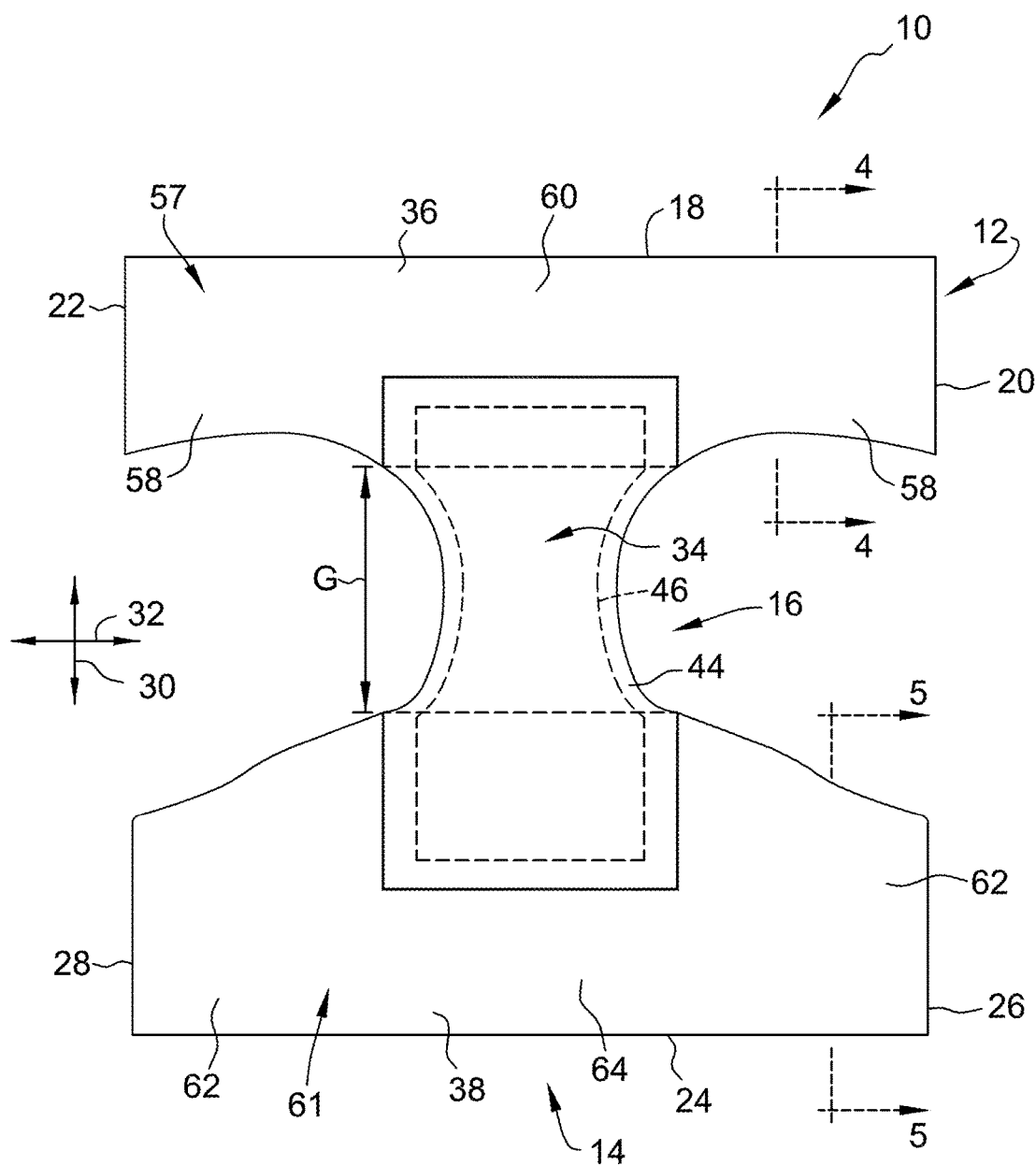
FIG. 1 is a top plan view of an absorbent article according to one suitable embodiment of the present disclosure in the form of a diaper pant, the diaper pant being illustrated in an unfolded and laid flat condition to show an inner surface of the diaper pant that faces the wearer when the diaper pant is worn.
Figure 2:
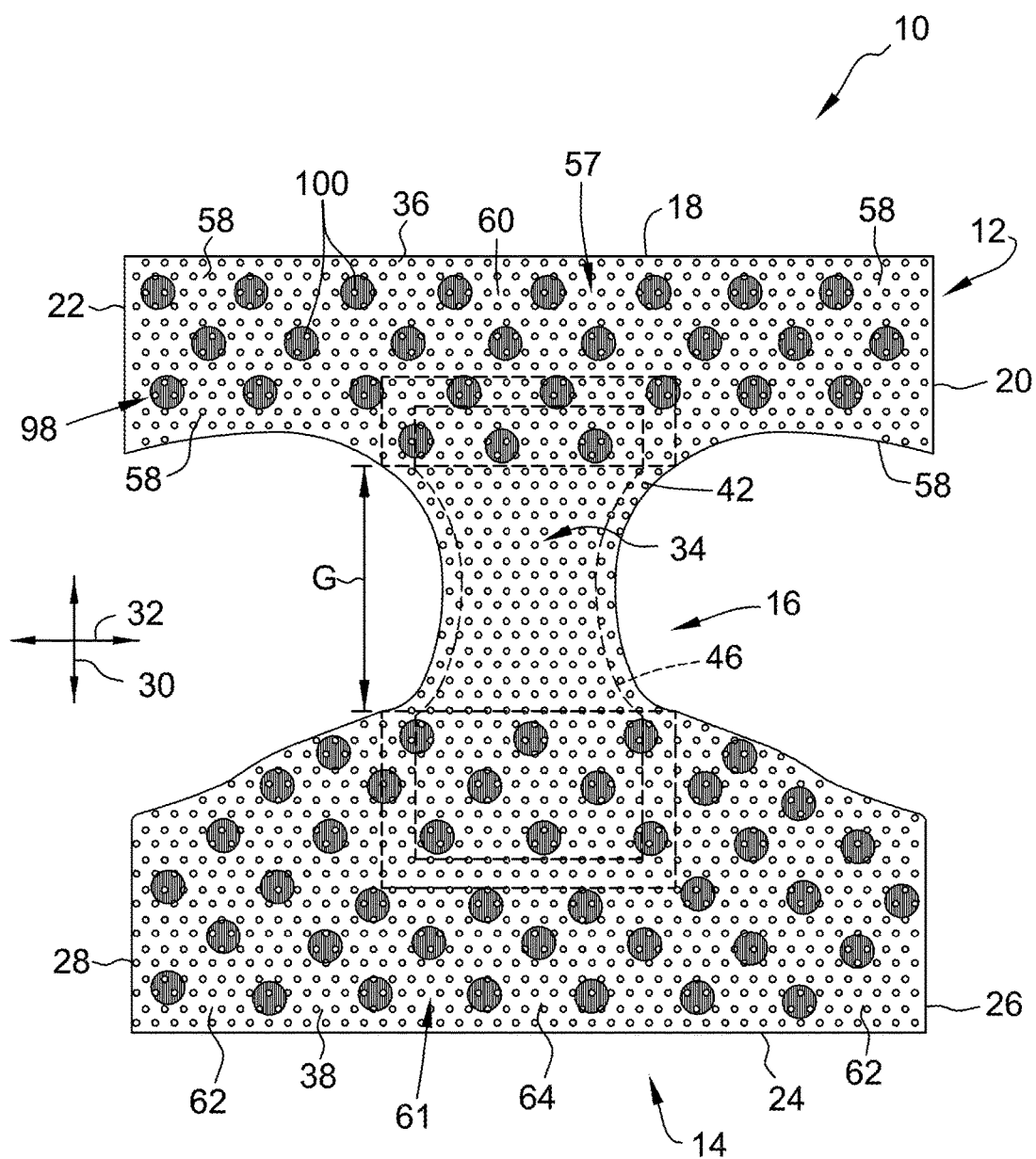
FIG. 2 is a bottom plan view of the diaper pant in an unfolded and laid flat condition to show an outer surface of the diaper pant that faces away from the wearer when the diaper pant is worn.
Figure 3:
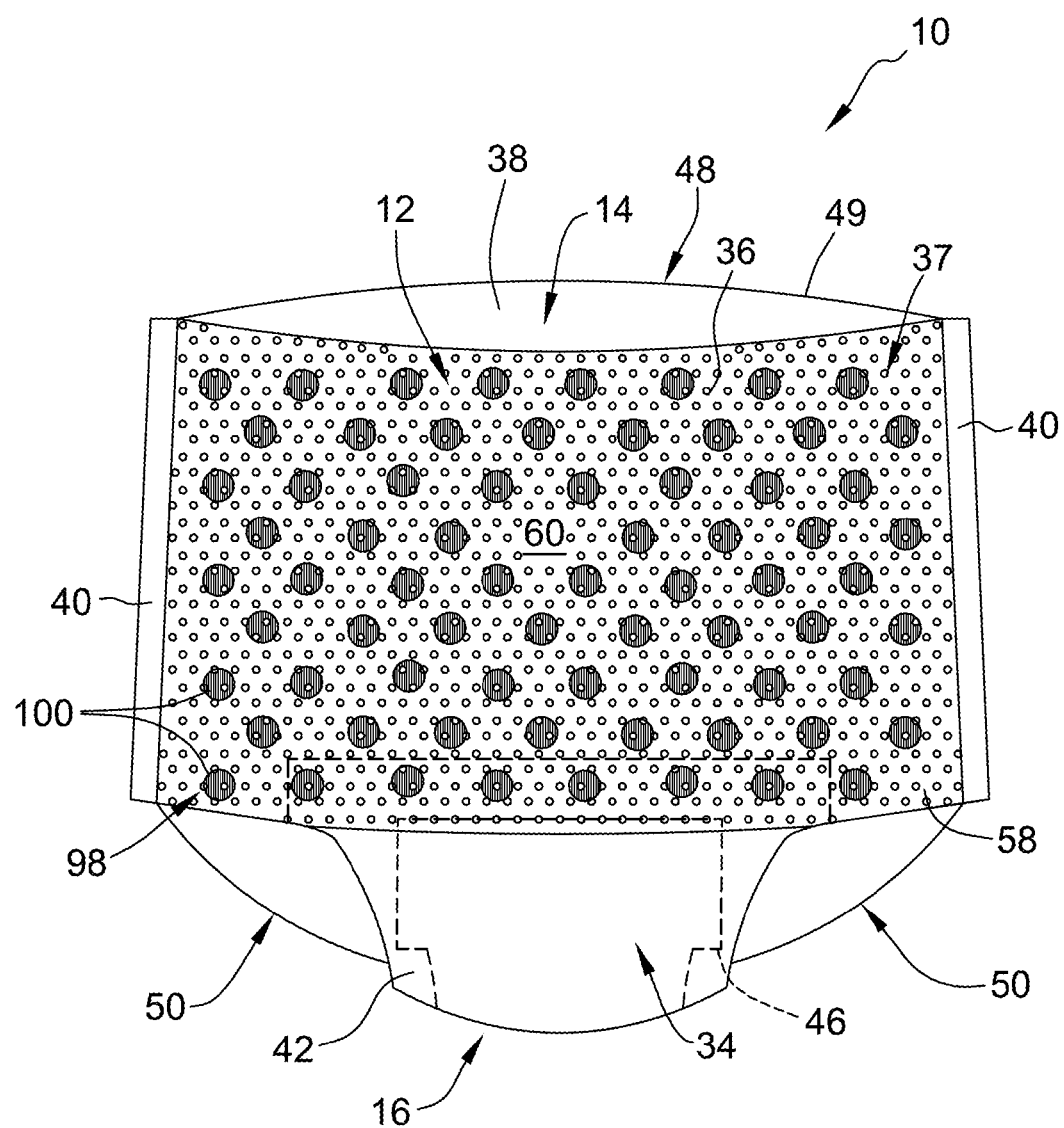
FIG. 3 is a front view of the diaper pant in the wear configuration.

With reference now to the drawings, FIGS. 1-3 illustrate one suitable embodiment of an absorbent article of the present disclosure in the form of a diaper pant, indicated generally at 10. While the present disclosure will be made in the context of the diaper pant 10, it should be understood that aspects of the present disclosure are applicable to other absorbent articles, such as, for example, refastenable diapers, adult incontinence garments, children's training pants, swim diapers, feminine care articles and the like.

In one suitable embodiment, the diaper pant 10 is a disposable absorbent article. As used herein, the term "disposable absorbent article" refers to articles which absorb and contain body exudates and which are intended to be discarded after a limited period of use. The articles are not intended to be laundered or otherwise restored for reuse. The articles can be placed against or in proximity to the body of a wearer to absorb and contain various exudates discharged from the body. It is understood that in other suitable embodiments, the diaper pant 10 (or more broadly, the absorbent article) can be reusable. That is, the absorbent article can be intended for multiple uses without departing from some aspects of this disclosure.

FIG. 1 illustrates the diaper pant 10 in an unfolded and laid flat condition to show an inner surface of the diaper that faces the wearer when the diaper is worn. FIG. 2, on the other hand, illustrates the diaper pant 10 in an unfolded and laid flat condition to show an outer surface of the diaper pant 10 that faces away from the wearer when the diaper is worn.

With reference still to FIGS. 1 and 2, the diaper pant 10 has a longitudinal direction 30 and a lateral direction 32. In the longitudinal direction 30, the diaper pant 10 defines a front region 12, a back region 14, and a crotch region 16 extending between and connecting the front region 12 and the back region 14.

In the front region 12, the diaper pant 10 has a front edge 18 and transversely opposed first and second front side edges 20, 22. A back edge 24 and transversely opposed first and second back side edges 26, 28 are located in the back region 14 of the diaper pant 10. In the illustrated embodiment, the front edge 18 and the back edge 24 are straight edges. That is, the front edge 18 and the back edge 24 are substantially free from curves, bends, angles, notches or irregularities. It is understood, however, that the front edge 18 and/or the back edge 24 can be cut in any suitable shape as is known in the art (e.g., arcuate).

The diaper pant 10 includes a central absorbent assembly, indicated generally at 34, that extends longitudinally from the front region 12 through the crotch region 16 to the back region 14. The central absorbent assembly 34 of the illustrated embodiment comprises an outer cover 42 and a bodyside liner 44 connected to the outer cover 42 in a superposed relation by suitable means such as adhesives, ultrasonic bonds, thermal bonds, pressure bonds, or combinations thereof. An absorbent structure 46 is disposed between the outer cover 42 and the bodyside liner 44.

The front and back regions 12, 14 of the diaper pant 10 are constructed of separate pieces of elastic laminate 36, 38 that are interconnected via the absorbent assembly 34. That is, the front region 12 is formed by a piece of elastic laminate 36 and the back region 14 is formed by a separate piece of elastic laminate 38. In the illustrated embodiment, each piece of laminate 36, 38 is attached to the outer cover 42 of the absorbent assembly 34 by suitable means such as adhesives, ultrasonic bonds, thermal bonds, pressure bonds, or combinations thereof. In other suitable embodiments, the elastic laminates 36, 38 may be joined to other portions of the central absorbent assembly 34, such as the bodyside liner 44. As seen in FIGS. 1 and 2, the laminate 36 forming the front region 12 is spaced from the laminate 38 forming the back region 14 to define a gap G. The absorbent assembly 34 spans the gap G and connects the laminate 36 forming the front region 12 to the laminate 38 forming the back region 14.

The laminate 36 used to form the front region 12 defines a front panel 57 including a pair of laterally opposite front side portions 58 extending outward from the absorbent assembly 34 at the front region 12, and a front central portion 60 disposed between the front side portions 58. The laminate 38 used to form the back region 14 defines a back panel 61 including a pair of laterally opposite back side portions 62 extending outward from the absorbent assembly 34 at the back region 14, and a back central portion 64 disposed between the back side portions 62.

As seen in FIG. 3, the laminate 36 used to form the front region 12 is joined to the laminate 38 used to form the back region 14 via a pair of non-refastenable butt (or fin) seams 40 to define a pull-on, pant-like configuration of the diaper pant 10 having a waist opening, indicated at 48, and two leg openings, indicated at 50. More specifically, each front side portion 58 is joined to a respective back side portion 62 via one of the non-refastenable butt seams 40.

With the diaper pant 10 in the pull-on, pant-like configuration, illustrated in FIG. 3, the front region 12 comprises the portion of the diaper pant 10 which, when worn, is positioned at least in part on the front of the wearer while the back region 14 comprises the portion of the diaper pant 10 which is positioned at least in part on the back of the wearer. The crotch region 16 of the diaper pant 10 comprises the portion of the diaper pant 10 which is positioned between the legs of the wearer and covers the lower torso of the wearer. The front and back side portions 58, 62 comprise the portions of the diaper pant 10 (and more particularly of the front and back regions 12, 14) which, when worn, are positioned on the hips of the wearer.

As seen in FIG. 3, the laminates 36, 38 cooperatively define an elastic laminate waist assembly, indicated at 37, that defines the waist opening 48 of the diaper pant 10, and is configured to fully encircle the waist of the wearer. The elastic laminate waist assembly 37 includes the front panel 57 and the back panel 61. As described in more detail herein, the waist assembly 37 is sufficiently water-vapor permeable to provide a healthy and comfortable product for the wearer, but is also sufficiently liquid impermeable to inhibit bodily fluids from leaking through the waist assembly 37.

The central absorbent assembly 34 is configured to contain and/or absorb exudates discharged from the wearer. The outer cover 42 suitably comprises a material which is substantially liquid impermeable. The outer cover 42 can be a single layer of liquid impermeable material, but more suitably comprises a multi-layered laminate structure in which at least one of the layers is liquid impermeable. For instance, the outer cover 42 can include a liquid permeable outer layer and a liquid impermeable inner layer that are suitably joined together by an adhesive, ultrasonic bonding, thermal bonding, pressure bonding, or combinations thereof. Suitable adhesives can be applied continuously or intermittently as beads, a spray, parallel swirls, or the like. The liquid permeable outer layer can be any suitable material, including materials that provide a generally cloth-like texture. The outer layer may also be made of those materials of which the liquid permeable bodyside liner 44 is made. While it is not a necessity for the outer layer to be liquid permeable, it is suitable that it provides a relatively cloth-like texture to the wearer.

The inner layer of the outer cover 42 can be both liquid and vapor impermeable, or it may be liquid impermeable and vapor permeable. The inner layer can be manufactured from a thin plastic film, although other flexible liquid impermeable materials may also be used. The inner layer, or the liquid impermeable outer cover 42 when a single layer, prevents waste material from wetting articles, such as bed sheets and clothing, as well as the wearer and caregiver.

If the outer cover 42 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 42. One suitable "breathable" material is composed of a microporous polymer film or a nonwoven fabric that has been coated or otherwise treated to impart a desired level of liquid impermeability.

It is also contemplated that the outer cover 42 may be stretchable, and more suitably elastic. In particular, the outer cover 42 is suitably stretchable and more suitably elastic in at least the transverse, or circumferential direction of the pant 10. In other embodiments the outer cover 42 may be stretchable, and more suitably elastic, in both the transverse and the longitudinal direction.

The liquid permeable bodyside liner 44 is illustrated as overlying the outer cover 42 and absorbent structure 46, and may, but need not, have the same dimensions as the outer cover 42. The bodyside liner 44 is suitably compliant, soft feeling, and non-irritating to the wearer's skin. The bodyside liner 44 is also sufficiently liquid permeable to permit liquid body exudates to readily penetrate through its thickness to the absorbent structure 46. Further, the bodyside liner 44 can be less hydrophilic than the absorbent structure 46 to present a relatively dry surface to the wearer and permit liquid to readily penetrate through its thickness. The hydrophilic/hydrophobic properties can be varied across the length, width and/or depth of the bodyside liner 44 and absorbent structure 46 to achieve the desired wetness sensation or leakage performance.

The bodyside liner 44 can be manufactured from a wide selection of web materials, such as porous foams, reticulated foams, apertured plastic films, woven and nonwoven webs, or a combination of any such materials. For example, the bodyside liner 44 may comprise a meltblown web, a spunbonded web, or a bonded-carded-web composed of natural fibers, synthetic fibers or combinations thereof. The bodyside liner 44 may be composed of a substantially hydrophobic material, and the hydrophobic material may optionally be treated with a surfactant or otherwise processed to impart a desired level of wettability and hydrophilicity. The surfactant can be applied by any conventional means, such as spraying, printing, brush coating or the like. The surfactant can be applied to the entire bodyside liner 44 or can be selectively applied to particular sections of the bodyside liner 44, such as the medial section along the longitudinal center line.

The bodyside liner 44 may also be stretchable, and, more suitably, it may be elastomeric. In particular, the bodyside liner 44 is suitably stretchable and more suitably elastomeric in at least the lateral or circumferential direction 32 of the pant 10. In other embodiments the bodyside liner 44 may be stretchable, and more suitably elastomeric, in both the lateral direction 32 and the longitudinal direction 30.

The absorbent structure 46 is suitably compressible, conformable, non-irritating to a wearer's skin, and capable of absorbing and retaining liquids and certain body wastes. For example, the absorbent structure 46 may comprise cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof.

The materials may be formed into a web structure by employing various conventional methods and techniques. For example, the absorbent structure 46 may be formed by a dry-forming technique, an air forming technique, a wet-forming technique, a foam-forming technique, or the like, as well as combinations thereof. Furthermore, the absorbent structure 46 may itself encompass multiple layers in a Z-direction (e.g., thickness) of the absorbent structure 46. Such multiple layers may take advantage of differences in absorbent capacity, such as by placing a lower absorbent capacity material layer closer to the bodyside liner 44 and a higher absorbent capacity material closer to the outer cover 42. Likewise, discrete portions of a single-layered absorbent structure may encompass higher capacity absorbents, and other discrete portions of the structure may encompass lower capacity absorbents.

Superabsorbent material is suitably present in the absorbent structure 46 in an amount of from about 0 to about 100 weight percent based on total weight of the absorbent structure 46. The absorbent structure 46 may suitably have a density within the range of about 0.10 to about 0.60 grams per cubic centimeter. Superabsorbent materials are well known in the art and can be selected from natural, synthetic, and modified natural polymers and materials. The superabsorbent materials can be inorganic materials, such as silica gels, or organic compounds, such as crosslinked polymers. Typically, a superabsorbent material is capable of absorbing at least about 10 times its weight in liquid, and preferably is capable of absorbing more than about 25 times its weight in liquid.

The absorbent structure 46 may alternatively comprise a coform material. The term "coform material" generally refers to composite materials comprising a mixture or stabilized matrix of thermoplastic fibers and a second non-thermoplastic material. As an example, coform materials are made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic absorbent materials, treated polymeric staple fibers and the like. Any of a variety of synthetic polymers may be utilized as the melt-spun component of the coform material. For instance, in certain aspects, thermoplastic polymers can be utilized. Some examples of suitable thermoplastics that can be utilized include polyolefins, such as polyethylene, polypropylene, polybutylene and the like; polyamides; and polyesters. In one aspect, the thermoplastic polymer is polypropylene.

In one suitable embodiment, the absorbent structure 46 is stretchable so as not to inhibit the stretchability of other components to which the absorbent structure may be adhered, such as the outer cover 42 and the bodyside liner 44. After being formed or cut to a desired shape, the absorbent structure 46 may be wrapped or encompassed by a suitable wrap (not shown) that aids in maintaining the integrity and shape of the absorbent structure 46.

The absorbent assembly 34 may also include a surge management layer (not shown) located adjacent the absorbent structure 46 (e.g., between the absorbent structure 46 and the bodyside liner 44) to help decelerate and diffuse surges or gushes of liquid that may be rapidly introduced into the absorbent structure 46 of the diaper pant 10 by the wearer. Desirably, the surge management layer can rapidly accept and temporarily hold the liquid prior to releasing the liquid into the storage or retention portions of the absorbent structure 46. Examples of suitable surge management layers are described in U.S. Pat. No. 5,486,166 issued Jan. 23, 1996 to Bishop et al.; U.S. Pat. No. 5,490,846 issued Feb. 13, 1996 to Ellis et al.; and U.S. Pat. No. 5,820,973 issued Oct. 13, 1998 to Dodge, II et al., the entire disclosures of which are hereby incorporated by reference.

The absorbent assembly 34 may also include a pair of containment flaps (not shown) that extend longitudinally along the absorbent assembly 34 and are adapted to provide a barrier to the lateral flow of body exudates as is known in the art. The containment flaps can be connected to the bodyside liner 44 or other components of the absorbent assembly 34. Suitable configurations of the containment flaps are described, for example, in U.S. Pat. No. 5,599,338 issued Feb. 4, 1997, to K. Enloe, the entirety of which is incorporated herein by reference.

Figure 4:
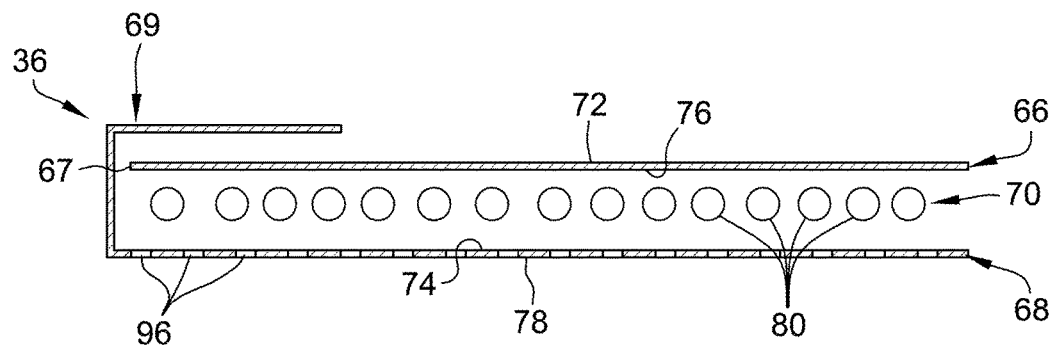
FIG. 4 is a cross-section of the diaper pant taken along line "4-4" in FIG. 1.

With reference to FIG. 4, the laminate 36 used to form the front region 12 comprises a multi-layer construction including an inner or body-facing layer 66, an outer or garment-facing layer 68, and an elastic layer 70 disposed between the body-facing layer 66 and the garment-facing layer 68. The body-facing layer 66 and the garment-facing layer 68 each include, respectively, a body-facing side 72, 74 and a garment-facing side 76, 78. The garment-facing side 76 of the body-facing layer 66 is connected to the body-facing side 74 of the garment-facing layer 68 by suitable means such as adhesives, ultrasonic bonds, thermal bonds, pressure bonds, or combinations thereof. In the illustrated embodiment, an upper portion 69 of the garment-facing layer 68 is folded over a top edge 67 of the body-facing layer 66. The upper portion 69 is connected to the body-facing side 72 of the body-facing layer 66 to close the top edge 49 of the waist opening 48 (FIG. 3), and enclose the elastic layer 70 between the body-facing layer 66 and the garment-facing layer 68.

The body-facing layer 66 is constructed from a non-apertured nonwoven material. Suitable nonwovens include single layer nonwovens, such as spunbond webs, and nonwoven laminates. In one suitable embodiment, the body-facing layer 66 comprises a spunbond/spunbond/spunbond ("SSS") laminate. In another suitable embodiment, the body-facing layer 66 comprises at least one meltblown layer positioned between two or more spunbond layers to form a spunbond/meltblown/spunbond ("SMS") laminate. In one particular embodiment, the body-facing layer 66 comprises a spunbond/spunbond/meltblown/meltblown/spunbond laminate ("SSMMS"). The nonwoven laminate may have other configurations and possess any desired number of meltblown and spunbond layers, such as spunbond/meltblown/meltblown/spunbond laminates ("SMMS"), spunbond/meltblown laminates ("SM"), etc. In addition to or as an alternative to meltblown and spunbond webs, a variety of other nonwoven webs may also be used to form the body-facing layer 66 including, for example and without limitation, through-air bonded carded webs, thermally bonded carded webs, wet-laid webs, coform webs, and hydraulically entangled webs.

The body-facing layer 66 is liquid-impermeable and vapor permeable. That is, the body-facing layer 66 permits vapors to escape from the interior of the disposable absorbent article, while still preventing liquids from passing through the body-facing layer 66. The body-facing layer 66 may be treated or otherwise processed to impart a desired level of liquid impermeability to the body-facing layer 66.

The elastic layer 70 is attached to at least one of the body-facing layer 66 and the garment-facing layer 68 to impart a desired level of elasticity to the laminate 36. The elastic layer may be attached to the body-facing layer 66 and/or the garment-facing layer 68 by any suitable means including, for example, adhesives. The elastic layer 70 can be stretched and then adhered to one or both of the body-facing layer 66 and the garment-facing layer 68, or adhered to one or both of the body-facing layer 66 and the garment-facing layer 68 when the layers 66, 68 are in a gathered state to impart a desired level of elasticity to the laminate 36. In other embodiments, the elastic layer 70 is adhered to one or both of the body-facing layer 66 and the garment-facing layer 68, and then elasticized or shrunk, for example with the application of heat, such that elastic retractive forces are imparted to the laminate 36.

The elastic layer 70 can be formed of a variety of suitable elastic materials, including sheets, strands, or ribbons of natural rubber, synthetic rubber, or thermoplastic elastomeric polymers. In the illustrated embodiment, the elastic layer 70 comprises a plurality of elastomeric strands 80 extending in the lateral direction 32 (FIGS. 1 and 2) or circumferential direction (FIG. 3) of the diaper pant 10. In one suitable embodiment, the elastomeric strands 80 comprise dry-spun coalesced multifilament spandex elastomeric strands sold under the trade name LYCRA® and available from Invista of Wichita, Kansas, U.S.A. Other suitable materials from which the elastic layer 70 may be constructed include vertical filament laminate (VFL) materials, an example of which is described in U.S. Pat. No. 6,916,750 to Thomas et al., which is hereby incorporated by reference; apertured elastic films, examples of which are described in U.S. Pat. No. 7,803,244 issued Sep. 28, 2010 to Siqueira et al., and U.S. Pat. No. 8,361,913 issued Jan. 29, 2013 to Siqueira et al., both of which are hereby incorporated by reference, and other elastic laminates such as single- and dual-faced spandex laminates, stretch-bonded laminates (SBL), and continuous filament stretch-bonded laminates (CFSBL), examples of which are described in U.S. Pat. No. 5,385,775 issued Jan. 31, 1995 to Wright; U.S. Pat. No. 6,057,024 issued May 2, 2000 to Mleziva et al.; and U.S. Pat. No. 6,969,441 issued Nov. 29, 2005 to Welch et al., all of which are hereby incorporated by reference.

The garment-facing layer 68 is vapor permeable, and may be liquid permeable or liquid impermeable. The garment-facing layer 68 is constructed from an apertured nonwoven, such as a single layer nonwoven or a nonwoven laminate. In one suitable embodiment, the garment-facing layer 68 comprises a spunbond/spunbond/spunbond ("SSS") laminate. In another suitable embodiment, the garment-facing layer 68 comprises at least one meltblown layer positioned between two or more spunbond layers to form a spunbond/meltblown/spunbond ("SMS") laminate. In one particular embodiment, the garment-facing layer 68 comprises a spunbond/spunbond/meltblown/meltblown/spunbond laminate ("SSMMS"). The nonwoven laminate may have other configurations and possess any desired number of meltblown and spunbond layers, such as spunbond/meltblown/meltblown/spunbond laminates ("SMMS"), spunbond/meltblown laminates ("SM"), etc. In addition to or as an alternative to meltblown and spunbond webs, a variety of other nonwoven webs may also be used to form the body-facing layer 66 including, for example and without limitation, through-air bonded carded webs, thermally bonded carded webs, wet-laid webs, coform webs, and hydraulically entangled webs.

The body-facing layer 66 and the garment-facing layer 68 are joined together in face-to-face relationship by suitable means such as adhesives, ultrasonic bonding, thermal bonding, pressure bonding, or combinations thereof. Suitable adhesives, which can be applied continuously or intermittently as beads, a spray, parallel swirls, or the like, include elastomeric adhesives (i.e. materials capable of at least 75% elongation without rupture), such as aqueous-based styrene butadiene adhesives, neoprene, polyvinyl chloride, vinyl copolymers, polyamides, and ethylene vinyl terpolymers.

Figure 5:
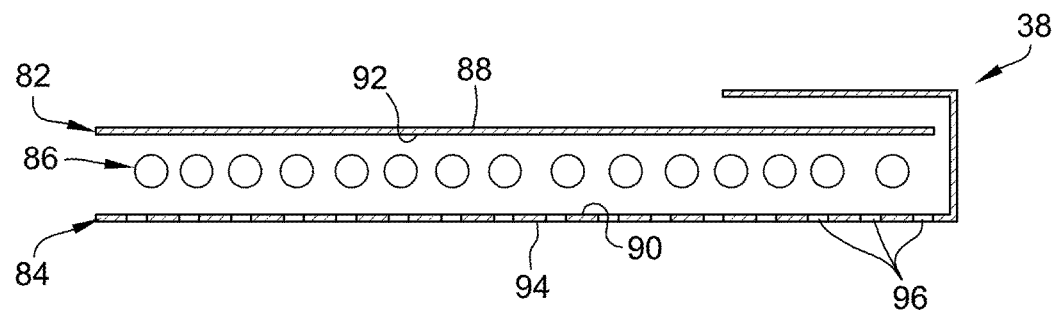
FIG. 5 is a cross-section of the diaper pant taken along line "5-5" in FIG. 1.

Referring to FIG. 5, the laminate 38 used to form the back region 14 has the same construction and configuration as the laminate 36 used to form the front region 12. That is, the laminate 38 comprises a multi-layer construction including an inner or body-facing layer 82, an outer or garment-facing layer 84, and an elastic layer 86 disposed between the body-facing layer 82 and the garment-facing layer 84. The body-facing layer 82 and the garment-facing layer 84 each include, respectively, a body-facing side 88, 90 and a garment-facing side 92, 94. The layers 82, 84, 86 of the laminate 38 may be constructed of the same materials as the layers 66, 68, 70 of the laminate 36 described above with reference to FIG. 4.

As seen in FIGS. 2, 4, and 5, the garment-facing layers 68, 84 have a plurality of apertures 96 formed therein to enhance the breathability of the laminates 36, 38. The apertures 96 define an apertured region in the garment-facing layers 68, 84 that fully encircles the waist opening 48 when the diaper pant 10 is in the wear configuration (shown in FIG. 3) to provide enhanced breathability along the entire waist assembly 37.

In one suitable embodiment, each of the apertures 96 is generally circular (when viewed from above or below—in plan view), but it is understood that the apertures can have any suitable shape (e.g., elliptical, square, triangular). In one suitable embodiment, the apertures 96 are generally circular and have a diameter between about 0.4 millimeters (mm) and about 4 mm and, more suitably, between about 1.0 mm and about 2.5 mm. In one particularly suitable embodiment, the apertures 96 have a diameter of about 1.2 mm. In another particularly suitable embodiment, the apertures 96 have a diameter about 2.0 mm. It is understood that the apertures 96 can have any suitable size and/or shape without departing from some aspects of this disclosure. It is also understood that the garment-facing layer 68, 84 of each laminate 36, 38 can have apertures 96 with different sizes and/or shapes. For example, different parts of the laminates 36, 38 can have different sized and/or shaped apertures 96.

The density of the apertures 96 in the garment-facing layers 68, 84 can range from about 6 apertures per square centimeter to about 36 apertures per square centimeter. In the illustrated embodiment, for example, the density of the apertures 96 is about 18 apertures per square centimeter. In another suitable embodiment, the density of the apertures 96 is about 12 apertures per square centimeter. It is understood that the apertures 96 in the garment-facing layers 68, 84 can have any suitable spacing and density. It is also understood that the spacing and/or density of the apertures 96 can vary in different parts of the garment-facing layers 68, 84. Thus, different parts of the garment-facing layers 68, 84 can have more or fewer apertures 96 than other parts without departing from some aspects of this disclosure.

Figure 6:
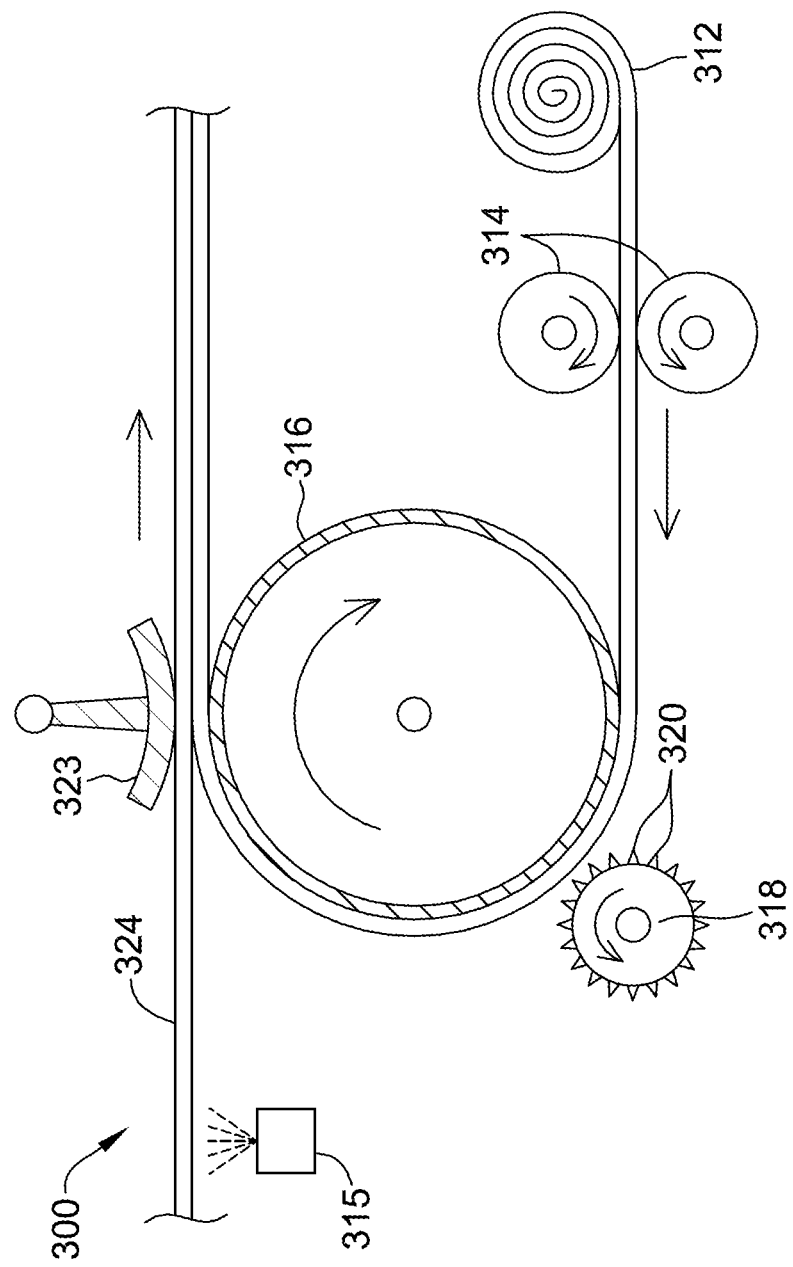
FIG. 6 is a schematic illustrating one suitable method of making an apertured elastic laminate suitable for use in the diaper pant of FIG. 1.

In one suitable embodiment, the apertures 96 in the garment-facing layers 68, 84 are suitably formed by needling. Needling is a process wherein a plurality of needles (or pins) is driven into or through the nonwoven layer in which the apertures are formed. With reference to FIG. 6, which illustrates one suitable embodiment of apparatus, indicated generally at 300, for making the laminate 36, 38, an incoming continuous web 312 of suitable nonwoven material may be fed to an anvil roll 316 via a web feeding assembly such as, e.g., one or more drive rollers 314. In the illustrated embodiment, the anvil roll 316 is a vacuum roll but it is contemplated that other suitable web handling devices can be used. The anvil roll 316 may internally contain or otherwise be connected to a suitable vacuum source (such as, e.g., a vacuum pump, a vacuum chamber, etc., not shown) which is capable of selectively applying a vacuum pressure (i.e., negative pressure) through one or more vacuum holes such that materials provided to the outer surface of the anvil roll are generally drawn to and secured against the outer surface. It is understood that any suitable backing roller can be used instead of or in combination with the anvil roll 316 to form the apertures 96 including, for example and without limitation, a matching roller, a deformable (e.g., rubber) roller, and a felt roller.

The apparatus 300 illustrated in FIG. 6 further comprises a needling roll 318 (broadly, "a needling station") comprising a plurality of needles 320. In one suitable embodiment, each of the needles 320 is generally conical in shape. It is understood, however, that the needles can have any suitable size or shape without departing from some aspects of this disclosure. The needles 320 are configured to penetrate the nonwoven web 312 a predetermined depth as the nonwoven web is carried by the anvil roll 316 past the needling roll 318. It is understood that other suitable methods (e.g., air or water jets) of deflecting fibers of the nonwoven web 312 in the z-direction (out of the x and y plane) and aperturing the nonwoven web 312 can be used without departing from some aspects of this disclosure.

As seen in FIG. 6, a continuously moving web 324 of material is delivered to the anvil roll 316. The web 324 of material may include the body-facing layer 66 or a composite web including the body-facing layer 66 bonded to one or more other layers, such as the elastic layer 70. In the illustrated embodiment, a suitable adhesive, is applied to the web 324 at an adhesive station 315 prior to or upon reaching the anvil roll 316. More specifically, the web 324 of material having adhesive thereon and the nonwoven web 312 are directed through a nip defined by the anvil roll 316 and a stomper 323 (or other suitable device, e.g., a roll). It is understood that the stomper 323 can be omitted. In such an embodiment, the nonwoven web 312 is adhered to the web 324 of material without the use of a nip.

As seen in FIGS. 2 and 3, the diaper pant 10 also includes a visual cue 98 configured to enhance the noticeability of the apertures 96 in the laminates 36, 38. In the illustrated embodiment, the visual cue 98 comprises a portion of each apertured layer being colored with a color that contrasts with the non-apertured layer. In particular, the visual cue 98 comprises a plurality of graphics 100 printed on the inner or body-facing side 74, 90 of each garment-facing layer 68, 84. It is understood that, additionally or alternatively, the graphics 100 may be printed on the inner or garment-facing side 76, 92 of the body-facing layers 66, 82. Each graphic 100 comprises a color that contrasts with the color of the body-facing layers 66, 82 to provide a visually contrasting background against which the apertures 96 are more readily visible. Although the graphics 100 are illustrated as having a generally circular shape, the graphics 100 may have any suitable shape and size that enables the graphics 100 to enhance the noticeability of the apertures 96. It is understood that the colored portion of the visual cue 98 may be disposed on either the body-facing layers 66, 82 or the garment-facing layers 68, 84. It is also contemplated that the colored portion may be disposed on a layer of material disposed between one of the body-facing layers 66, 82 and one of the garment-facing layers 68, 84. Although the colored portion is typically printed in an inner side of one of the body-facing layers 66, 82 and garment-facing layers 68, 84, it is understood that the colored portion may be printed on an outer side of one of the body-facing layers 66, 82 and garment-facing layers 68, 84. Further, the colored portion may be formed by means other than printing. In one suitable embodiment, for example, the visual cue 98 comprises a nonwoven panel colored in its entirety (e.g., using pigment).

Experiments

Twelve elastic laminate samples were prepared and tested for hydrostatic pressure, air permeability, bending stiffness, and burst strength as described below. The twelve elastic laminate samples tested consisted of four samples having a non-apertured garment-facing layer and a non-apertured body-facing layer, five samples having an apertured garment-facing layer and a non-apertured body-facing layer, and three samples having an apertured garment-facing layer and an apertured body-facing layer.

The construction of each sample, including the materials used for the body-facing layer and the garment-facing layer, and the aperture hole size and density for the apertured layers, is provided below in Table 1.

TABLE 1

| | Construction of Test Samples | | | |
|---|---|---|---|---|
| Sample No. | Garment-Facing Layer | Body-Facing Layer | Aperture Size (diameter, in mm) | Aperture Density (#/cm$^2$) |
| 1 | non-apertured SSS web having a basis weight of 13 grams per square meter (gsm) | non-apertured SSS web having a basis weight of 13 gsm | N/A | N/A |
| 2 | apertured SSS web having a basis weight of 13 gsm | non-apertured SSS web having a basis weight of 13 gsm | 1.2 | 18 |
| 3 | apertured SSS web having a basis weight of 13 gsm | apertured SSS web having a basis weight of 13 gsm | 1.2 | 18 |
| 4 | non-apertured SSMMS web having a basis weight of 12 gsm | non-apertured SSMMS web having a basis weight of 13 gsm | N/A | N/A |
| 4a | non-apertured SSMMS web having a basis weight of 12 gsm | non-apertured SSMMS web having a basis weight of 12 gsm | N/A | N/A |
| 5 | apertured SSMMS web having a basis weight of 12 gsm | non-apertured SSMMS web having a basis weight of 13 gsm | 1.2 | 18 |
| 5a | apertured SSMMS web having a basis weight of 12 gsm | non-apertured SSMMS web having a basis weight of 12 gsm | 1.2 | 18 |
| 6 | apertured SSMMS web having a basis weight of 12 gsm | apertured SSMMS web having a basis weight of 12 gsm | 1.2 | 18 |
| 6a | apertured SSMMS web having a basis weight of 12 gsm | apertured SSMMS web having a basis weight of 12 gsm | 1.2 | 18 |
| 7 | apertured SSMMS web having a basis weight of 12 gsm | non-apertured SSMMS web having a basis weight of 13 gsm | 1.2 | 18 |
| 8 | apertured SSMMS web having a basis weight of 12 gsm | non-apertured SSMMS web having a basis weight of 13 gsm | 2.0 | 12 |
| 9 | non-apertured SSMMS web having a basis weight of 13 gsm | non-apertured SSMMS web having a basis weight of 13 gsm | N/A | N/A |

Each sample included an elastic layer disposed between the garment-facing layer and the body-facing layer. The elastic layer in each sample comprised 15 strands of dry-spun coalesced multifilament spandex sold under the trade name LYCRA® and available from Invista of Wichita, Kansas, U.S.A, each having a decitex (g/1000 m) of about 540. The elastic strands were adhered to the body-facing layer and the garment-facing layer at an elongation of about 200% using a suitable elastomeric adhesive. The samples were tested with the elastic strands in a relaxed (i.e., unstretched) state.

Apertured layers having an aperture density of 18 apertures/cm$^2$ were apertured using a needle punch having 18 pins/cm$^2$. Apertured layers having an aperture density of 12 apertures/cm$^2$ were apertured using a needle punch having 12 pins/cm$^2$. A plurality of graphics was printed on the body-facing layer of Sample 7 to enhance the noticeability of the apertures in the garment-facing layer.

Hydrostatic Pressure Test

The Hydrostatic Pressure Test measures the liquid barrier properties of a fabric. The hydrostatic pressure of each test sample was determined using Federal Test Standard 191A, Method 5514, which is incorporated by reference herein. Federal Test Standard 191A, Method 5514 is well known and will not be set forth in detail herein. However, the test procedure is summarized as follows. The test head of a Textest FX-3000 Hydrostatic Head Tester, available from Schmid Corporation, having offices in Spartanburg, S.C., was filled with deionized water. The deionized water was maintained at a temperature of about 73.4±3.6° F. and about 50±5% relative humidity. A medium size head of 26 cm$^2$ was applied. A 4 inch by 4 inch (about 10.2 cm by 10.2 cm)

square specimen of each test sample material was placed such that the test head reservoir was completely covered. An 8 inch by 8 inch (20 cm×20 cm) piece of commercially available nylon net having a 3 mm (about 0.125 inches) mesh was placed between each specimen and the upper test head to support the specimen to prevent stretching of the specimen. The specimen was subjected to water pressure increased at a constant rate of 60 millibar (mbar) per minute until leakage through the specimen was observed. Hydrostatic pressure resistances were measured when a single drop was observed leaking through the specimen (1-Drop Hydrostatic Pressure Test) and when three drops were observed leaking through the specimen (3-Drop Hydrostatic Pressure Test). This test was repeated for 10 specimens of each test sample material. The hydrostatic pressure results for each specimen were averaged and recorded in millibars (mbar).

Air Permeability Test

The Air Permeability Test measures the rate of air-flow through a known dry specimen area. The air permeability of each sample was measured using a Textest FX3300 air permeability tester available from Schmid Corporation, having offices in Spartanburg, S.C.

A specimen from each test sample was cut and placed so that the specimen extended beyond the clamping area of the air permeability tester. The test specimens were obtained from areas of the sample that were free of folds, crimp lines, perforations, wrinkles, and/or any distortions that make them abnormal from the rest of the test material.

The tests were conducted in a standard laboratory atmosphere of 23±1° C. (73.4±1.8° F.) and 50+2% humidity. The instrument was turned on and allowed to warm up for at least 5 minutes before testing any specimens. The instrument was calibrated based on the manufacturer's guidelines before the test material was analyzed. The pressure sensors of the instrument were reset to zero by pressing the NULL RESET button on the instrument. Before testing, and if necessary between samples or specimens, the dust filter screen was cleaned, following the manufacturer's instructions. The following specifications were selected for data collection: (a) Unit of measure: cubic feet per minute (cfm); (b) test pressure: 125 Pascal (water column 0.5 inch or 12.7 mm); and (c) test head: 38 square centimeters (cm²). Since test results obtained with different size test heads are not always comparable, samples to be compared should be tested with the same size test head.

The NULL RESET button was pressed prior to every series of tests, or when the red light on the instrument was displayed. The test head was open (no specimen in place) and the vacuum pump was at a complete stop before the NULL RESET button was pressed.

Each specimen was placed over the lower test head of the instrument. The test was started by manually pressing down on the clamping lever until the vacuum pump automatically started. The Range Indicator light on the instrument was stabilized in the green or yellow area using the RANGE knob. After the digital display was stabilized, the air permeability of the specimen was displayed, and the value was recorded. The test procedure was repeated for 10 specimens of each sample, and the average value for each sample was recorded as the air permeability.

Bending Stiffness Test

The Bending Stiffness of each sample was measured using a KES Advanced Pure Bend Tester Model FB2-L, available from the Kato Tech Co, Ltd. of Japan. The KES Advanced Pure Bend Tester Model FB2-L measures the pure bending properties of a sample for a given range of curvature at ±0.4 cm$^{-1}$ with a constant speed at 0.5 cm$^{-1}$/s. The 'SENS' was set at 4 to give a full scale of bending moment of 80 grams-force centimeters (gf-cm). The bending through curvature 0 to 0.4 cm$^{-1}$ denotes as the forward bend while bending through curvature 0 to −0.4 cm$^{-1}$ denotes as the backward bend. The Bend Tester measures bending stiffness (B) in grams-force*cm²/cm (gf-cm²/cm). The bending stiffness is defined as the average slope of bending moment versus curvature in the forward and backward bend. In the forward bend, the slope is taken in curvature between 0.1 cm$^{-1}$ and 0.3 cm$^{-1}$, while in the backward bend the slope is taken in curvature between −0.1 cm$^{-1}$ and −0.3 cm$^{-1}$.

A 10 cm by 10 cm (about 3.9 inch by 3.9 inch) specimen was cut from each test sample, with two opposite sides of the specimen running parallel to a Machine Direction (MD) and two perpendicular sides of the specimen running parallel to a Cross Machine Direction (CD). Test specimens were selected from the sample material that were free from all folds, wrinkles, crimp lines, and of any distortions that would make the specimen abnormal from the rest of the sample. The bending stiffness of each test specimen was measured in MD such that MD of the specimen is perpendicular to the vertical front and back clamps in the Bend Tester. The back clamp was fixed at one location while the front clamp was moveable. The distance between the front and back clamps was at a default of 4 cm. The result of each material sample is the average of data from 5 specimens of test sample. The data was acquired using KES-FB System Measurement Program (KES-FB System FB2-L Only Ver. 7.9 W/For Win 98/NT/2000) by Kato Tech Co., LTD. of Japan.

Burst strength Test

The Burst Strength Test measures the amount of force required to burst (i.e., rupture) a test sample using a constant rate of extension (CRE) tensile tester. The burst strength of each sample was measured using an MTS Criterion Model 42 tensile tester commercially available from MTS Systems Corporation.

A 4 inch by 4 inch (101.6 mm×101.6 mm) test specimen was cut from each test sample, and placed in a clamping fixture having a circular opening defining the test area. A penetration assembly having a smooth, spherical probe tip was arranged perpendicular to and centered under the circular test area. The penetration assembly consisted of a spherical probe tip affixed to the end of a socket, which was secured to the tensile tester with a lock nut. The Burst Strength Test was carried out according to TAPPI T570 pm-00, using a test speed of 6 inches per minute and a load cell of 50 Newtons. The penetration assembly was raised at the specified test speed such that the spherical probe tip contacted and eventually penetrated the test specimen to the point of specimen rupture. The maximum force applied by the penetration assembly at the instant of specimen rupture was recorded as the burst strength in grams-force (gf). The average value from 10 specimens of each test sample was recorded.

Test Results

Test results for Hydrostatic Pressure, Air Permeability, Bending Stiffness, and Burst Strength Testing for each sample are provided below in Table 2.

TABLE 2

Results of Hydrostatic Pressure, Air Permeability, Bending Stiffness, and Burst strength Testing

| Sample No. | Hydrostatic Pressure (mbar) (1 drop) | Hydrostatic Pressure (mbar) (3 drops) | Air Permeability (cfm) | Bending Stiffness (gf-cm$^2$/cm) | Burst Strength (gf) |
|---|---|---|---|---|---|
| 1 | 8.8 | 9.5 | 607.2 | 0.311 | 4851.8 |
| 2 | 7.5 | 8.3 | 611.9 | 0.268 | 4591.7 |
| 3 | 4.0 | 4.5 | 678.3 | 0.211 | 4213.9 |
| 4 | 20.5 | 21.6 | 268.0 | 0.692 | 5465.0 |
| 4a | 22.1 | 23.4 | 235.2 | 0.629 | 4738.7 |
| 5 | 13.9 | 16.6 | 322.6 | 0.840 | 5142.5 |
| 5a | 16.2 | 20.0 | 280.2 | 0.494 | 4358.0 |
| 6 | 2.9 | 3.4 | 456.1 | 0.305 | 4152.4 |
| 6a | 4.3 | 4.8 | 381.0 | 0.289 | 3932.5 |
| 7 | 14.3 | 16.1 | 317.6 | 0.530 | 5582.7 |
| 8 | 13.0 | 16.0 | 321.2 | 0.661 | 4666.4 |
| 9 | 20.0 | 21.3 | 298.9 | 0.608 | 5483.4 |

The test results indicate that elastic laminate samples with an apertured garment-facing layer and a non-apertured body-facing layer have improved air permeability characteristics as compared to samples having no apertured layers, and improved hydrostatic pressure characteristics as compared to samples with an apertured garment-facing layer and an apertured body-facing layer. In other words, elastic laminate samples having an apertured garment-facing layer and a non-apertured body-facing layer provide a desirable level of air permeability while also providing a sufficient level of liquid impermeability to inhibit bodily fluids from leaking through the elastic laminate.

For example, Sample Nos. 1-3 were each constructed from an SSS web having a basis weight of 13 gsm. Sample No. 1 had no apertured layers, Sample No. 2 had 1 apertured layer, and Sample No. 3 had 2 apertured layers. Sample No. 1 had an air permeability of 607.2 cfm, whereas Sample No. 2 had an air permeability of 611.9 cfm. Sample No. 2 had a hydrostatic pressure of 7.5 mbar as determined by the 1-Drop Hydrostatic Pressure Test, whereas Sample No. 3 had a hydrostatic pressure of 4.0 mbar as determined by the 1-Drop Hydrostatic Pressure Test.

Sample Nos. 4a, 5a, and 6a were each constructed from an SSMMS web having a basis weight of 12 gsm. Sample 4a had no apertured layers, Sample No. 5a had 1 apertured layer, and Sample No. 6a had 2 apertured layers. Sample No. 4a had an air permeability of 235.2 cfm, whereas Sample No. 5a had an air permeability of 280.2 cfm. Sample No. 5a had a hydrostatic pressure of 16.2 mbar as determined by the 1-Drop Hydrostatic Pressure Test, whereas Sample No. 6a had a hydrostatic pressure of 4.3 mbar as determined by the 1-Drop Hydrostatic Pressure Test.

Further, the test results indicate that use of a single apertured layer in the elastic laminate did not have a significant impact on the burst strength of the test sample, whereas the use of two apertured layers did have a significant impact the burst strength of the sample.

For example, Sample No. 1 had a burst strength of 4851.8 gf. Sample No. 2, which had a single apertured layer, had a burst strength of 4591.7 gf, whereas Sample No. 3, which had two apertured layers, had a burst strength of 4213.9 gf.

Samples Nos. 4a, 5a, and 6a displayed similar results. Specifically, Sample No. 4a had a burst strength of 4738.7 gf. Sample 5a, which had a single apertured layer, had a burst strength of 4358.0 gf, whereas Sample 6a, which had two apertured layers, had a burst strength of 3932.5 gf.

In one suitable embodiment, the elastic laminates 36, 38 disclosed herein have a hydrostatic pressure of between about 4 mbar and about 20 mbar as determined by the 1-Drop Hydrostatic Pressure Test, and an air permeability of between about 310 cfm and about 620 cfm as determined by the Air Permeability Test. In one particularly suitable embodiment, the elastic laminates 36, 38 have a hydrostatic pressure of between about 4 mbar and about 20 mbar as determined by the 1-Drop Hydrostatic Pressure Test, and an air permeability of between about 310 cfm and about 400 cfm as determined by the Air Permeability Test. In another particularly suitable embodiment, the elastic laminates 36, 38 have a hydrostatic pressure of between about 4 mbar and about 20 mbar as determined by the 1-Drop Hydrostatic Pressure Test, and an air permeability of between about 550 cfm and about 620 cfm as determined by the Air Permeability Test.

In another suitable embodiment, the elastic laminates 36, 38 disclosed herein have a hydrostatic pressure of between about 7 mbar and about 17 mbar as determined by the 1-Drop Hydrostatic Pressure Test, and an air permeability of between about 260 cfm and about 690 cfm as determined by the Air Permeability Test. In one particularly suitable embodiment, the elastic laminates 36, 38 have a hydrostatic pressure of between about 10 mbar and about 17 mbar as determined by the 1-Drop Hydrostatic Pressure Test, and an air permeability of between about 260 cfm and about 690 cfm as determined by the Air Permeability Test. In another particularly suitable embodiment, the elastic laminates 36, 38 have a hydrostatic pressure of between about 13 mbar and about 15 mbar as determined by the 1-Drop Hydrostatic Pressure Test, and an air permeability of between about 260 cfm and about 690 cfm as determined by the Air Permeability Test.

In yet another suitable embodiment, the elastic laminates 36, 38 disclosed herein have a burst strength of between about 4000 gf and about 6000 gf and, more suitably, between about 4300 gf and about 5700 gf.

When introducing elements of the present invention or the preferred embodiment(s) thereof, the articles "a", "an", "the", and "said" are intended to mean that there are one or more of the elements. The terms "comprising," "including", and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An absorbent article having a front region, a back region, and a crotch region extending between and connecting the front region and the back region, the absorbent article comprising:

an absorbent assembly extending longitudinally between the front region and the back region, the absorbent assembly comprising an inner layer for facing a wearer, an outer layer for facing away from the wearer, and an absorbent structure disposed between the inner and outer layers; and a waist assembly including a front panel and a back panel both formed separately from each other and then attached to the absorbent assembly, the front panel extending along the front region and the back panel extending along the back region, the front and back panels defining a waist opening of the absorbent article when the article is in a wear configuration, wherein the front and back panels are fully formed from an elastic laminate comprising a non-apertured body-facing layer that is liquid-impermeable and vapor permeable, an apertured garment-facing layer that is vapor permeable, and an elastic layer disposed between the body-facing layer and at least the garment-facing layer.

2. The absorbent article as set forth in claim 1, wherein the front panel is attached to the absorbent assembly along the front region, and the back panel is attached to the absorbent assembly along the back region, the front panel being attached to the back panel by a pair of spaced-apart side seams to define the waist opening of the absorbent article.

3. The absorbent article as set forth in claim 1, wherein each of the body-facing layer and the garment-facing layer comprises at least one meltblown layer.

4. The absorbent article as set forth in claim 3, wherein at least one of the body-facing layer and the garment-facing layer comprises a spunbond/meltblown laminate.

5. The absorbent article as set forth in claim 1, wherein each of the body-facing layer and the garment-facing layer comprises at least one of a spunbond laminate, a through-air bonded carded web, and a thermally bonded carded web.

6. The absorbent article as set forth in claim 1, wherein the garment-facing layer has a plurality of apertures formed therein, each aperture having a diameter of between about 0.4 mm and about 4.0 mm, the plurality of apertures defining an aperture density of between 6 apertures per square centimeter and 36 apertures per square centimeter.

7. The absorbent article as set forth in claim 1, wherein the elastic layer comprises a plurality of elastic strands extending circumferentially around the waist opening when the article is in the wear configuration.

8. The absorbent article as set forth in claim 1, wherein the absorbent article further comprises a visual cue configured to enhance the noticeability of the apertures formed in the garment-facing layer.

9. The absorbent article as set forth in claim 8, wherein the visual cue comprises at least a portion of one of the body-facing layer and the garment-facing layer being colored with a color that contrasts with the other of the body-facing layer and the garment-facing layer.

10. The absorbent article as set forth in claim 1, wherein the elastic laminate has a burst strength of between about 4000 grams-force and about 6000 grams-force as determined by the Burst Strength Test.

11. The absorbent article as set forth in claim 3, wherein each of the body-facing layer and the garment-facing layer comprises a spunbond/spunbond/meltblown/meltblown/spunbond laminate.

12. The absorbent article as set forth in claim 1, wherein the apertured garment-facing layer comprises an upper portion folded over a top edge of the non-apertured body-facing layer.

13. An absorbent article having a front region, a back region, and a crotch region extending between and connecting the front region and the back region, the absorbent article comprising:

an absorbent assembly extending longitudinally between the front region and the back region, the absorbent assembly comprising an inner layer for facing a wearer, an outer layer for facing away from the wearer, and an absorbent structure disposed between the inner and outer layers; and a waist assembly including a front panel and a back panel both formed separately from each other and then attached to the absorbent assembly, the front panel extending along the front region and the back panel extending along the back region, the front and back panels defining a waist opening of the absorbent article when the article is in a wear configuration, wherein the front and back panels are fully formed from an elastic laminate comprising a non-apertured body-facing layer that is liquid-impermeable and vapor permeable, an apertured garment-facing layer that is vapor permeable, and an elastic layer disposed between the body-facing layer and at least the garment-facing layer, wherein the elastic laminate has a hydrostatic pressure of between about 4 millibar and about 20 millibar as determined by the 1-Drop Hydrostatic Pressure Test, and an air permeability of between about 310 cubic feet per minute and about 620 cubic feet per minute as determined by the Air Permeability Test.

14. The absorbent article as set forth in claim 13, wherein the elastic laminate has an air permeability of between about 310 cubic feet per minute and about 400 cubic feet per minute as determined by the Air Permeability Test.

15. The absorbent article as set forth in claim 13, wherein the elastic laminate has an air permeability of at least about 550 cubic feet per minute as determined by the Air Permeability Test.

16. The absorbent article as set forth in claim 13, wherein the front panel is attached to the back panel by a pair of spaced-apart side seams to define the waist opening of the absorbent article.

17. The absorbent article as set forth in claim 13, wherein the elastic laminate has a burst strength of between about 4000 grams-force and about 6000 grams-force as determined by the Burst Strength Test.

18. An absorbent article having a front region, a back region, and a crotch region extending between and connecting the front region and the back region, the absorbent article comprising:

an absorbent assembly extending longitudinally between the front region and the back region, the absorbent assembly comprising an inner layer for facing a wearer, an outer layer for facing away from the wearer, and an absorbent structure disposed between the inner and outer layers; and a waist assembly including a front panel and a back panel both formed separately from each other and then attached to the absorbent assembly, the front panel extending along the front region and the back panel extending along the back region, and the front and back panels defining a waist opening of the absorbent article when the article is in a wear configuration, wherein the front and back panels are fully formed from an elastic laminate comprising a non-apertured body-facing layer that is liquid-impermeable and vapor permeable, an apertured garment-facing layer that is vapor permeable, an elastic layer disposed between the body-facing layer and at least the garment-facing layer, wherein the elastic laminate has a hydrostatic pressure of between about 7 millibar and about 17 millibar as determined by the 1-Drop Hydrostatic Pressure Test, and an air permeability of between about 260 cubic feet per minute and about 690 cubic feet per minute.

19. The absorbent article as set forth in claim 18, wherein the elastic laminate has a hydrostatic pressure of at least about 10 millibar as determined by the 1-Drop Hydrostatic Pressure Test.

20. The absorbent article as set forth in claim 19, wherein each of the body-facing layer and the garment-facing layer comprises at least one meltblown layer.

21. The absorbent article as set forth in claim 20, wherein each of the body-facing layer and the garment-facing layer comprises a spunbond/spunbond/meltblown/meltblown/spunbond laminate.

22. The absorbent article as set forth in claim 18, wherein the front panel is attached to the back panel by a pair of spaced-apart side seams to define the waist opening of the absorbent article.

23. The absorbent article as set forth in claim 18, wherein the elastic laminate has a burst strength of between about 4000 grams-force and about 6000 grams-force as determined by the Burst Strength Test.

* * * * *